(12) United States Patent
Lennernäs et al.

(10) Patent No.: US 8,124,118 B2
(45) Date of Patent: Feb. 28, 2012

(54) COMPOSITION COMPRISING BIODEGRADABLE HYDRATING CERAMICS FOR CONTROLLED DRUG DELIVERY

(75) Inventors: Hans Lennernäs, Uppsala (SE); Bo Lennernäs, Uddevalla (SE); Jonas Hugosson, Kungsbacka (SE); Niklas Axén, Järlåsa (SE)

(73) Assignee: Lidds AB, Helsingborg (SE)

( * ) Notice: Subject to any disclaimer, the term of this patent is extended or adjusted under 35 U.S.C. 154(b) by 943 days.

(21) Appl. No.: 10/576,857

(22) PCT Filed: Oct. 21, 2004

(86) PCT No.: PCT/EP2004/012060
§ 371 (c)(1),
(2), (4) Date: Oct. 7, 2008

(87) PCT Pub. No.: WO2005/039537
PCT Pub. Date: May 6, 2005

(65) Prior Publication Data
US 2009/0036392 A1    Feb. 5, 2009

Related U.S. Application Data

(60) Provisional application No. 60/561,875, filed on Apr. 14, 2004.

(30) Foreign Application Priority Data

Oct. 22, 2003    (SE) ..................................... 0302782

(51) Int. Cl.
*A61K 31/56* (2006.01)
*A61K 31/7088* (2006.01)
*A61P 35/00* (2006.01)

(52) U.S. Cl. .......................... 424/423; 514/44; 514/178
(58) Field of Classification Search .......................... None
See application file for complete search history.

(56) References Cited

U.S. PATENT DOCUMENTS

| | | | |
|---|---|---|---|
| 4,218,255 A | 8/1980 | Bajpai et al. | |
| 4,891,225 A | 1/1990 | Langer et al. | |
| 5,156,623 A | 10/1992 | Hakamatsuka et al. | |
| 5,162,117 A * | 11/1992 | Stupak et al. | 424/475 |
| 5,164,186 A | 11/1992 | Tsuru et al. | |
| 5,614,206 A | 3/1997 | Randolph et al. | |
| 5,626,862 A | 5/1997 | Brem et al. | |
| 5,683,725 A | 11/1997 | Malik et al. | |
| 5,756,127 A | 5/1998 | Grisoni et al. | |
| 5,807,567 A | 9/1998 | Randolph et al. | |
| 6,030,636 A | 2/2000 | Randolph et al. | |
| 6,251,139 B1 | 6/2001 | Lin et al. | |
| 6,277,391 B1 | 8/2001 | Seo et al. | |
| 6,391,336 B1 | 5/2002 | Royer | |
| 6,479,418 B2 * | 11/2002 | Li et al. | 501/81 |
| 6,497,901 B1 | 12/2002 | Royer | |
| 6,630,486 B1 | 10/2003 | Royer | |
| 6,689,375 B1 | 2/2004 | Wahlig et al. | |
| 6,869,976 B2 | 3/2005 | Royer | |
| 2003/0082232 A1 | 5/2003 | Lee et al. | |
| 2003/0147936 A1 | 8/2003 | Sahadevan | |
| 2003/0158598 A1 * | 8/2003 | Ashton et al. | 623/1.42 |
| 2003/0170307 A1 * | 9/2003 | Royer | 424/484 |
| 2004/0020893 A1 | 2/2004 | Drake et al. | |

FOREIGN PATENT DOCUMENTS

| | | |
|---|---|---|
| DE | 19620117 | 7/1997 |
| EP | 0061108 | 9/1982 |
| EP | 0159089 | 10/1985 |
| EP | 0192068 | 8/1986 |
| EP | 0376331 | 7/1990 |
| EP | 0508653 | 10/1992 |
| EP | 0947489 | 10/1999 |
| WO | WO 97/47334 | 12/1997 |
| WO | WO 99/15150 | 4/1999 |
| WO | WO 00/45734 | 8/2000 |
| WO | WO 01/05706 | 1/2001 |
| WO | WO 0241844 | 5/2002 |
| WO | WO 02/087649 | 11/2002 |
| WO | 03/180344 * | 2/2003 |
| WO | WO 03/011214 | 2/2003 |
| WO | WO 03/011957 | 2/2003 |
| WO | WO 03/024316 | 2/2003 |
| WO | WO 03/043607 | 5/2003 |
| WO | WO 03/059409 | 7/2003 |
| WO | WO 03/092759 | 11/2003 |
| WO | WO 04/000276 | 12/2003 |
| WO | WO 04/000277 | 12/2003 |
| WO | WO 2004/028580 | 4/2004 |

\* cited by examiner

*Primary Examiner* — Robert A Wax
*Assistant Examiner* — Danah Al-Awadi
(74) *Attorney, Agent, or Firm* — Thorpe North & Western LLP

(57) ABSTRACT

The present invention relates to a drug carrier composition comprising i) one or more biodegradable hydrating ceramics ii) one or more expandable agents, and iii) sorbed aqueous medium which in solid form has a ruptured structure. The function of the expandable agent is to create a ruptured structure in the solidified composition, either a foam-like structure or a disintegrated structure where it is split into a large number of parts, particles, units, granules or pieces, so as to obtain an enlarged apparent surface area that is exposed to degradation or erosion upon administration. Suitable substances to obtain this surface enlarging effect are gas-forming agents or swelling agents, gelling agents or disintegrants, here referred to as expandable agents. The expandable agents may be bioresorbable or non-bioresorbable.

49 Claims, 2 Drawing Sheets

COMPOSITION COMPRISING BIODEGRADABLE HYDRATING CERAMICS FOR CONTROLLED DRUG DELIVERY

FIELD OF THE INVENTION

The present invention relates to novel compositions suitable as carriers for therapeutically, prophylactically and/or diagnostically active substances to the human body or any other mammals. The compositions of the invention are based on biodegradable hydrating ceramics and are applicable for several drug delivery purposes; for example, for targeted treatment to specific part(s) of the body such as diseased organs or for localized treatment of e.g. cancer such as, e.g., prostate cancer e.g. through targeted and local release of hormonal and anti-hormonal agents.

The compositions of the invention, including the active substance (s), can be applied locally with minimally invasive techniques, and a sustained (controlled) local release profile of the drug over a prolonged period of time can be obtained.

Such local and sustained delivery of active substances (e.g. drug substances) optimises the local concentration-time profile of the active substances and their local pharmacological effects, and minimises the systemic exposure and thus reduces the side-effects, and hence increases the safety and utility of the active substance and the pharmaceutical composition containing the active substance. In addition the compliance of the therapy is enhanced.

BACKGROUND OF THE INVENTION

In drug delivery there is a need for improved formulation techniques that enables a targeted and/or localised delivery of active drug substances to the body. For instance in the drug treatment of tumours or other diseases in local tissues, procedures and formulations to optimise the local effects of the drugs and reduce the spectrum of side effects are still needed. Drug release implants that are implanted with minimally invasive surgery are also they attractive since they reduce the need for open surgery.

Ceramic substances like e.g. calcium sulphate have been suggested as implant materials for controlled release of active substances (see e.g. Royer U.S. Pat. No. 6,391,336, U.S. Pat. No. 6,630,486, US 2003/0170307). In order to obtain a slower release of the active substance from the ceramics, Royer uses a complexing agent that is a polymeric substance that forms a complex with the active substance, whereby a slower release may be obtained.

However, the present inventors have found another method to adjust the release rate of the active substance, which method involves sealing of the inherent micro-porous structure within the composition in order to ensure that the release primarily takes place via erosion or biodegradation of the implanted composition.

Moreover, a suitable way of controlling the erosion or biodegradation rate is described, based on ensuring a structure of the ceramic characterised by an increased surface area towards to surrounding environment, whereby the erosion or biodegradation of the composition is increased (due to the increased apparent surface area). Accordingly, a better adjustment method is achieved, whereby the primary adjustment factor lies in the more open structure, e.g. a ruptured structure like a foam-like structure or a disintegrated structure, obtained in a composition according to the invention. The increased surface area towards the body fluids and tissues is achieved using additives here referred to as expandable agents.

INTRODUCTION

Drug Delivery Systems Based on Biodegradable Hydrating Ceramics

This invention is related to carrier materials of hydrating ceramics with additives that regulate the drug release rate to span over prolonged periods of time.

The present invention benefits from several of the inherent properties of hydrating ceramics. Hydrating ceramics are materials that solidify as a result of chemical reactions between a ceramic powder and water. Common hydrating ceramics are based on calcium silicates (main component in Portland cement), calcium sulphates (the main component of gypsum), and calcium phosphates (e.g. hydroxyapatite, the mineral of bone tissue). The hydrating ceramics are often used as fine-grained powders, which are mixed with water to achieve mouldable pastes, and additives to optimise properties like viscosity and curing time.

As the powder is mixed with water, chemical processes take place involving the formation of hydrate phases containing chemically bonded water. The formed hydrates constitute the binding phase that holds together (cements) the hence formed solid material. The hydration process and thereby the properties of the hydrate materials is controlled by additives.

It is inherent to the hydrating ceramics, that they show some degree of micro-porosity after curing. This is because of the limited degree of hydrate formation and water absorption during the hydration. Depending on type of ceramic, and the amount of water added, as well as the original grain size of the ceramic powder, the pore size of a cured ceramic is normally between 1 and 10 microns and the total porosity in the order of 10-30%. Pores between 10 and 100 microns and porosities between 30 and 50% are also conceivable. This porosity is referred to as the micro-porosity in the present context. The micro-porosity constitutes a structure of openings between the original ceramic grains. This micro-porosity allows for water to be sorbed by capillary forces into the hydrophilic material and thereby creates a diffusion path for water solvable or soluble molecules. There is however no or limited rheological flow through the micro-porosity, and tissues cannot grow into it.

Several biodegradable ceramic compositions have been developed for drug delivery purposes. Either the drug is added as a powder, suspension, solution, emulsion or liquid to a paste of ceramic powder and water, and is embedded in the ceramic as it cures. Alternatively, a porous cured body of the ceramic is soaked in a liquid that contains the dissolved drug.

In orthopedics hydroxyapatite, calcium phosphate or calcium sulphate systems are used in the form of beads granules, scaffolds and mouldable in-vivo curing pastes, both to provide mechanical stability at the site of a fracture, but also to leak therapeutic substances, e.g. antibiotics and bone growth factors, to surrounding tissue.

The biodegradable ceramics have many favourable properties as carriers for drugs in slow release applications, such as non-toxic components normally occurring in living tissues, a high degree of biocompatibility, ease of production, etc.

Resorbable calcium phosphate based ceramics are described in U.S. Pat. No. 6,027,742. Biodegradable calcium sulphate materials are described in WO 03/082158, and WO 00/45734.

However, the release rate of drug substances from these ceramic carriers is difficult to tune. For both calcium phosphate and calcium sulphate based drug delivery compositions, the release time span generally becomes too high for many drug systems, in the order of 1-3 weeks or less. The present invention provides compositions, wherein the release rate can be prolonged to 1-6 months or more.

Normally, the drug release rate from a ceramic implant is controlled by two factors: First, the release of drugs through the water filled micro-porosity of the implanted composition. The water filled micro-porosity is a path for drugs and a solvable drug may be transported from the implant interior to the surrounding tissues, by e.g. diffusion, convection or flow. Second, the release rate is caused by the degradation or erosion of the implant itself, which as it proceeds exposes the implant interior and the encapsulated drug to the environment.

The present invention provides compositions, which provide prolonged drug release rates from biodegradable implants based on hydrating ceramics, wherein the release mechanism primarily is based on the overall erosion of the ceramics.

SUMMARY OF THE INVENTION

The present invention provides in a first aspect, a drug carrier composition comprising
i) one or more biodegradable hydrating ceramics
ii) one or more expandable agents, and
iii) sorbed aqueous medium
which in solid form has a ruptured structure.

The drug carrier composition is the basis in a pharmaceutical composition of the invention. Accordingly, in a second aspect, the invention relates to a pharmaceutical composition comprising
i) one or more biodegradable hydrating ceramics
ii) one or more expandable agents,
iii) sorbed aqueous medium, and
iv) one or more therapeutically, prophylactically and/or diagnostically active substances,
which in solid form has a ruptured structure.

As apparent from the above, the drug carrier composition as well as the pharmaceutical composition may be in fluid, liquid, semi-solid or solid form. As will be explained in detail herein, a composition is suitably applied in a paste or another semi-solid form (preferably injectable form), but it must relatively quickly solidify upon administration in order to remain at the desired site (e.g. organ). The solidification/hydration may take place inside or out-side of the body. Accordingly, within the scope of the present invention are both the injectable compositions as well as the solidified compositions.

A practical use of the compositions of the invention may be to initialize the hydrating process immediately before administration to a patient. Accordingly, a composition containing the ingredients in powder or particulate form is also within the scope of the present invention and intended to be admixed with water or an aqueous medium immediately before administration. Thus, in a third aspect, the invention relates to a composition in particulate form for use in the preparation of a drug carrier composition as defined in any of claims 1-24 or a pharmaceutical composition as defined in any of claims 25-69, the composition comprising
i) one or more biodegradable hydrating ceramics in powder form
ii) one or more expandable agents, and
iii) optionally, one or more therapeutically, prophylactically and/or diagnostically active substances.

The present invention also provides a method for preparation of a pharmaceutical composition as defined in any of claims 25-69.

As mentioned above the invention relates to compositions, which are suitable for local drug delivery over prolonged periods of time such as, e.g., in the order of 1-6 months or longer. As an example this can be used for treatment of prostate cancer through local release of hormonal and anti-hormonal agents, including for example androgens and anti-androgens, in the prostate gland.

The present invention provides a mouldable pasty or putty containing the drugs of choice, which can be positioned with standard surgical instruments (needles, tubings, etc) at the selected site in the body. The paste may posses a high X-ray, ultrasonic and magnetic resonance visibility. Once positioned, the biodegradable composition solidifies in vivo and hence forms an implant of mechanical integrity. The implant (i.e. the solidified pharmaceutical composition) provides a sustained release of the therapeutic agents for a prolonged period of time (1-6 months or more) to the surrounding tissues.

The treatment composition prior to solidification consists essentially of a hydrating ceramic powder, the active substances of choice, expandable agents, like gas-forming agents or disintegrants to enhance the external surface exposed to the tissues, an aqueous medium and if necessary pore-sealing agents and other additives. After solidification, the implant is characterised by a matrix based on hydrated ceramics, a micro-porosity that is largely filled (sealing of the pores) to prevent communication and exchange of substances with the implant interior, and the selected drug being encapsulated in the implant.

DETAILED DISCLOSURE OF THE INVENTION

As mentioned above, the present invention provides a drug carrier composition comprising
i) one or more biodegradable hydrating ceramics
ii) one or more expandable agents; and
iii) sorbed aqueous medium
which in solid form has a ruptured structure.

A ruptured structure is an open structure, wherein the inner and outer surfaces are interrupted by openings or fractures. Examples are foam-like structures created by expandable agents like gas-forming agents, or disintegrated structures created by disintegrants.

The one or more expandable agents may either contribute to the ruptured structure by creating a foam-like structure with openings, wherein at least 50% or more have a largest width of at least about 0.1 mm, or by disintegration of solidified material into two or more parts. These two or more parts have an external surface area that is at least about twice as large as that of the composition before disintegration such as, e.g. at least about ten times as large, at least about a hundred times as large, or about a thousand times as large or more. Openings in the foam-like structure can be seen by microscopy (cf. FIG. 2 herein). The openings may of course be of varying size, but it is desirable that a least every second (corresponding to 50%) on an average basis has a largest width of at least about 0.1 mm. Especially, at least 60% (6 out of 10 on an average basis) such as, e.g., at least 70% (7 out of 10 on an average basis), at least 75% (15 out of 20 on an average basis), at least 80% (8 out of 10 on an average basis), at least 85% (17 out of 20 on an average basis) or at least 90% (9 out of 10 on an average basis) of the openings have a largest width of at least about 0.1 mm. In preferred aspects, the openings have a largest width of at least about 0.2 mm such as, e.g. at least about 0.3 mm, at least about 0.4 mm, at least about 0.5 mm, or they have a largest width of at least about 0.6 mm such as, e.g. at least about 0.8 mm, at least about 1.0 mm, or from about 0.1 mm to about 2 mm such as, e.g., from about 0.3 mm to about 1.5 mm or from about 0.5 mm to about 1.5 mm. Alternatively, the surface area of an opening in cross sectional view having a largest width of at least about 0.1 mm is at least about $3 \times 10^{-8}$ m$^2$ such as, e.g. at least about $5 \times 10^{-8}$ m$^2$, at least $1 \times 10^{-7}$ m$^2$, at least about $5 \times 10^{-7}$ m$^2$, at least about $1 \times 10^{-6}$ m$^2$, or about $5 \times 10^{-6}$ m$^2$ or more.

In an embodiment of the invention the drug carrier composition further comprises one or more therapeutically, prophylactically and/or diagnostically active substances. In a preferred embodiment of the invention the therapeutically, prophylactically and/or diagnostically active substance in the pharmaceutical composition is an anti-cancer agent. The active substance may be homogeneously dispersed in the biodegradable hydrating ceramic.

A drug carrier composition and a pharmaceutical composition according to the invention may have a shape like e.g. beads, pellets, tubes, polygons, spheres, stars, cubes, etc.

In the present context the term 'controlled release' is used synonymous with the terms 'sustained release', 'modified release', and 'prolonged release', and intended to mean a release of an active substance according to a predetermined pattern, e.g. zero order release, or other orders of release, with or without an initial burst release and/or an initial lag time before start of a release.

In the present context the term 'release' is used synonymous with the term 'delivery'.

In the following is given details with respect to the individual ingredient.

The Hydrating Ceramic

According to the invention, an implant for sustained drug delivery is achieved from a composition based one or several hydrating ceramics. Suitable biodegradable hydrating ceramic for use in a composition of the invention is selected from the group consisting of non-hydrated or hydrated calcium sulphate, calcium phosphate, calcium carbonate, calcium fluoride, calcium silicate, magnesium sulphate, magnesium phosphate, magnesium carbonate, magnesium fluoride, magnesium silicate, barium sulphate, barium phosphate, barium carbonate, barium fluoride, barium silicate, or mixtures thereof.

Of prime interest are calcium sulphates such as non-hydrated or hydrated calcium sulphate. In its most basic form, the hydrating ceramic of the composition is calcium sulphate. The calcium sulphate may be of the alfa- or beta-structure and be non-hydrated, hemihydrates or fully hydrated.

However, as described above also calcium phosphates, calcium carbonates, calcium fluorides and calcium silicates, alone or in combination, and with various amounts of bonded water, are relevant to the invention. In a more general form of the invention, the calcium of these ceramics may be replaced by magnesium or barium. Any combination of these ceramics is of relevance to the invention.

The biodegradable hydrating ceramic is added to the composition in the form of a powder such as a fine-grained powder, with a mean particle size of at the most about 75 μm such as, e.g., at the most about 50 μm, at the most about 25 μm or at the most about 10 μm.

According to the invention, the biodegradable hydrating ceramic is normally used with additives that regulate the release rate by optimising the micro-porosity of the cured implant (pore-sealing agents) and the external surface of the implant (by use of expandable agents), which is exposed to the surroundings. A reduced micro-porosity reduces the leaching of drugs from the implant through water that penetrates the porosity. An increased surface of the implant increases its erosion rate and reduces the sensitivity to dimensions of the implant.

Any concentration of hydrated ceramic in the treatment composition falling between 10 and 99 vol. %, as measured on the solidified implant, is of relevance to the invention. Most preferably the solidified treatment composition contains between 70 and 95 vol. % of hydrated ceramic.

A drug carrier composition according to the invention may be constituted in such a way, that the hydrating ceramics does not cure while the composition is mixed or during an implantation by e.g. injection in a patient, but readily cures at body temperature after injection. The drug carrier composition may solidify after a suitable time period of about 20 min or less such as, e.g. about 15 min or less, about 10 min or less or about 5 min or less when stored at 37° C. Optionally the composition may be prepared and cured outside the body, and implanted as solid pieces Optionally, the composition of the invention also contains non-hydrating ceramic and metallic additives. The purpose of such additional component is increased radio-opacity, improved mechanical strength or solidification rate control. Established radio-opacity additives are barium salts or metals such as gold, zirconium or tantalum and their oxides.

Release Rate Control

Normally, the drug release rate from a cured hydrating ceramic implant is basically controlled by two factors: First, the leaching of water solvable drugs from the implant interior to the surroundings caused by a transport of water through the micro-porosity of the implant. Second, the degradation of the ceramic implant itself in the environment of the implantation site, which over time erodes the material and exposes the implant interior and new drug to the environment.

The erosion rate of the ceramic material is controlled by numerous factors including: the type ceramic material and its solubility in a body liquid, the size of the surface exposed to the tissue and the type/composition of tissues and body fluids that the implant is surrounded by. Different hydrating ceramics differ strongly in their inherent chemical stability and degradation rate; calcium sulphates are generally considered as quickly degradable (4-6 weeks in bone tissue), calcium phosphates as more stable (many months or years depending on the type of calcium phosphate), whereas hydrated calcium silicates are even more stable.

The surface exposed to the body environment may be controlled by creating openings of sufficient size for tissue and cells to invade the implant, i.e. larger than 100 microns, alternatively with an additive that disintegrates and splits the implant into numerous pieces/segments that act as multiple release sites. The openings may be created by the action of expandable agents.

Expandable Agents

As mentioned above, a drug carrier composition according to the invention comprises one or more expandable agents. The function of the expandable agent is to create a ruptured structure in the solidified composition, either a foam-like structure or a disintegrated structure where it is spit into a large number of parts, particles, units, granules or pieces, so as to obtain an enlarged apparent surface area that is exposed to degradation or erosion upon administration. Suitable substances to obtain this surface enlarging effect are gas-forming agents or swelling agents, gelling agents or disintegrants, here referred to as expandable agents. The expandable agents may be bioresorbable or non-bioresorbable.

To obtain a controllable release rate through erosion of the ceramic-based carrier material, a large surface area envisaging the surrounding environment is essential. This area is the sum of the outer area $A_{out}$, or the geometrical area of the implant, defining the extension of the implant in the body; and the inner area $A_{in}$ from e.g. a foam structure or a disintegrated structure of multiple parts or particles caused by e.g. a swelling additive in the structure. For a controllable release, the outer area $A_{out}$ must be much smaller than the inner area, i.e. $A_{out} \ll A_{in}$.

Examples of expandable agents that are gas-forming agents are e.g. alkali metal carbonates including sodium carbonate and potassium carbonates; alkali metal hydrogen carbonates including sodium hydrogen carbonate and potassium hydrogen carbonate; and hydrogen peroxide.

Suitable examples of expandable agents that are swelling agents, gelling agents or disintegrants are e.g. alginic acid, alginates, cellulose and cellulose derivatives e.g. of various molecular weights, including calcium carboxymethylcellulose, sodium carboxymethylcellulose, crospovidone, hydroxypropylcellulose, hydroxypropylmethylcellulose (HPMC), low substituted hydroxypropylcellulose (L-HPC), microcrystalline cellulose, pectins, polyethylene glycols, polyethylene oxides, polyvinylpyrrolidone, starches e.g. of various molecular weights including corn starch, rice starch, potato starch, and mixtures thereof.

A mixture of gas-forming agent(s) and swelling agent(s), gelling agent(s) or disintegrant(s) may also be suitable for use in the present context.

Normally, the concentration of the expandable agent in the composition is at least about 0.1% w/w such as, e.g., at least about 0.2% w/w, at least about 0.3% w/w, at least about 0.4% w/w or at least about 0.5% w/w or from about 0.1% to about 10% w/w such as, e.g., from about 0.1% to about 5% w/w, from about 0.1% to about 2.5% w/w or from about 0.1% to about 1% w/w.

In an embodiment of the invention the one or more biodegradable hydrating ceramics and the expandable agent are homogeneously dispersed in water so that the hydrating ceramic and/or the expandable agent sorbs water.

With respect to the final water content, a composition according to the invention normally has a concentration of sorbed aqueous medium of at the most about 60% w/w such as, e.g., at the most about 50% w/w, at the most about 45% w/w, at the most about 40% w/w or at the most about 30% w/w of the total composition.

In the present context, the term "sorption" is uses as a common expression for either "adsorption" or "absorption" or both.

Micro-porosity

As mentioned above, the one or more biodegradable hydrating ceramics may have a microporous structure. In a preferred embodiment of the invention, at least part of the microporous structures is sealed with a pore-sealing agent. More specifically, at least 50% such as, e.g., 60% or more, 70% or more, 80% or more or 90% or more of the microporous structures is sealed with a pore-sealing agent.

Examples of pore-sealing agents suitable for use in the present context are hydrophobic agents, hydrophilic agents and water-absorbing agents. Pore-sealing agents that reduce the micro-porosity and produce a sealing of the ceramic implant are:

Hydrophobic or poorly water soluble additives added to the treatment composition as liquids, suspensions or dispersions that fill the micro-porosity and prevent water from penetrating and leach the drugs from the implant. Examples of such additives are: oils, rubbers, waxes, hydrocarbons, cellulose derivatives, etc. specific examples are silicon oil or silicon rubber, waxes, paraffinic hydrocarbons, polyvinylalcohols, ethyl cellulose. Amounts of these additives up to 30 vol. %, as measured on the cured implant is of relevance to the invention.

Water soluble or hydrophilic additives that fill porosity with a thick or gel like consistency and prevent the water circulation through the implant. Examples of such additives are: methylcellulose, hyaluronic acid, dextran, polyethylene glycol (PEG). Amounts of these additives up to 30 vol. %, as measured on the cured implant is of relevance to the invention.

Water absorbing agents, which bind the excessive water that is not consumed in the hydration of the ceramic, may be highly water absorbing ionic salt additives. Examples of such additives are: water glasses, silica gel, sodium phosphate, etc. Amounts of these additives up to 30 vol. %, as measured on the cured implant is of relevance to the invention.

Hydrating ceramics with a high water absorption during hydration. Most interesting to the invention are calcium silicates and calcium aluminates. However, also additions of calcium phosphates, calcium carbonates, calcium fluorides and calcium silicates, alone or in combination are relevant to the invention. The calcium may be replaced by magnesium or barium. Amounts of these additives up to 30 vol. %, as measured on the cured implant is of relevance to the invention.

Normally, the concentration of the pore-sealing agent in the composition is about 30% w/w or less such as, e.g., about 25% w/w or less or about 20% or less in the final composition.

Optionally, the composition may also contain rheology control additives such as poly-carboxylic acids or poly-acrylic acids; methylcellulose, dextran or hyaluronic acid.

Optionally, the treatment composition may also contain a bio-adhesive component, such as suitable polymer, which helps the therapeutic agent to stay adhered to the surrounding tissue over a prolonged period of time.

The composition contains water or an aqueous medium as a principal solvent.

Property Profile of Composition

Apart from carrying and releasing the therapeutic agent, the composition of the invention is such that it also provides a property profile including:

a viscosity allowing injectability through standard syringes, needles, tubing systems and cannulae for minimally invasive application of the composition to the selected site;

in-situ solidification properties so that the composition solidifies within 5 to 20 minutes after final mixing providing increased mechanical and chemical resistance after application at the selected site to make the composition stay constrained and resist the movements of the tissues and the flow of body fluids.

a high visibility with radioscopy (X-ray), ultrasonic and magnetic resonance imaging techniques. Monitoring facilitates the accurate application of the treatment composition at the selected site, as well as the continuous observation of the biodegradation rate for individualised dosing.

a sustained release profile for the active substance; e.g. for the treatment of prostate cancer a suitable substance is 2-hydroxy-flutamide that fulfils the therapeutic concentration which is within the interval 0.001-1000 µM, preferably 0.01-100 µM or more preferably 0.05-5.0 µM, and the treatment time for one dose is at least 3-6 months or more.

In a specific embodiment the active substance is controlled released from the composition. More specifically, at the most about 10% w/w of the active substance contained in the composition is released 5 days or more after implantation to a human, and/or at the most about 50% w/w of the active substance contained in the composition is released 1 month or more after implantation to a human, and/or at the most about 75% w/w of the active substance contained in the composition is released 1.5 month or more such as, e.g., 2 month or more after implantation to a human, and/or at most about 100% w/w of the active substance contained in the composition is released 2 month or more such as 2.5 month or more or 3 month or more after implantation to a human.

In an alternative embodiment at the most about 10% w/w of the active substance contained in the composition is released after 2 days or more—when tested in an in vitro dissolution test according to Ph.Eur. (paddle), and/or at the most about 50% w/w of the active substance contained in the composition is released after 1 month or more—when tested in an in vitro dissolution test according to Ph.Eur. (paddle), and/or at the most about 75% w/w of the active substance contained in the composition is released after 1.5 month or more such as, e.g., 2 month or more—when tested in an in vitro dissolution test according to Ph.Eur. (paddle), and/or at the most about 100% w/w of the active substance contained in the composition is released after 2 month or more such as 2.5 month or more or 3 month or more—when tested in an in vitro dissolution test according to Ph.Eur. (paddle).

Drugs of Relevance to the Invention

The invention is also applicable to therapeutic agents in a broad sense, including androgens or derivates thereof (e.g. testosterone), antiandrogens (cyproteron, flutamide, hydroxyflutamide, bicalutamide, nilutamide) or derivatives thereof, oestrogens or derivates thereof, anti-oestrogens (e.g. tamoxifen, toremifen) or derivates thereof, gestagens or derivates thereof, antigestagens or derivatives thereof, oligonucleotides, progestagens or derivates thereof, gonadotropin-releasing hormone or analogues or derivates thereof, gonadotropin inhibitors or derivates thereof, adrenal and prostate enzyme synthesis inhibitors (such as α-reductase inhibitors), membrane efflux and membrane transport proteins (such as PSC 833, verapamil), and other cytostatic agents, immune system modulators and angiogenesis inhibitors alone or in combinations.

The invention also includes any other suitable pharmaceutical agents applied in soft tissues or organs for local or systemic sustained drug release. The sustained drug release compositions of the invention can also be explored in other treatments e.g.: pain, neurological diseases (Alzheimer, Parkinson), autoimmune diseases, immunological diseases, and diseases responding to immunological and immunomodulating therapy (hepatitis, MS, tumours), infections, inflammations, metabolic diseases, obesitas, diseases in the uro-genital tract, cardiovascular diseases (including blood pressure), hematopoietic, anticoagulant, thrombolytic and antiplatelet diseases, chemotherapy of parasitic infections, microbial diseases and neoplastic diseases, hypercholesterolemia, dyslipidemia, hematopoetic diseases, respiratory diseases (asthma, chronical lung obstruction), diseases of the kidney, gastrointestinal diseases, liver diseases, hormonal disruption, replacement and substitution, vitamins replacement and substitution. Examples of active drug substances from various pharmacolocial classes for the use in the present clinical context include e.g. antibacterial agents, antihistamines and decongestants, anti-inflammatory agents, antiparasitics, antivirals, local anaesthetics, antifungals, amoebicidals or trichomonocidal agents, analgesics, antianxiety agents, anticlotting agents, antiarthritics, antiasthmatics, anticoagulants, anticonvulsants, antidepressants, antidiabetics, antiglaucoma agents, antimalarials, antimicrobials, antineoplastics, antiobesity agents, antipsychotics, antihypertensives, auto-immune disorder agents, anti-impotence agents, anti-Parkinsonism agents, anti-Alzheimers agents, antipyretics, anticholinergics, anti-ulcer agents, anorexics, beta-blockers, beta-2 agonists, alpha receptor antagonists and agonists, blood glucose-lowering agents, bronchodilators, agents with effect on the central nervous system, cardiovascular agents, cognitive enhancers, contraceptives, cholesterol-reducing agents, agents against dyslipidemia, cytostatics, diuretics, germicidals, H-2 blockers, hormonal agents, anti-hormonal agents, hypnotic agents, inotropics, muscle relaxants, muscle contractants, physic energizers, sedatives, sympathomimetics, vasodilators, vasoconstrictors, tranquilizers, electrolyte supplements, vitamins, uricosurics, cardiac glycosides, membrane efflux inhibitors, membrane transport protein inhibitors, expectorants, purgatives, contrast materials, radiopharmaceutical, imaging agents, peptides, enzymes, growth factors, vaccines, mineral trace elements, etc.

The therapeutically, prophylactically and/or diagnostically active drug substance(s) may also be in the form of a pharmaceutically acceptable salt, solvate or complex thereof or in any suitable crystalline or amorphous form or in the form of a prodrug.

The drug load of the implant composition, i.e. the amount of active substance in the composition, can vary within wide limits. The concentration of the active substance in the composition may be in the range from about 0.01% w/w to about 50% w/w such as, e.g. from about 0.01% w/w to about 40% w/w, from about 0.05% w/w to about 30% w/w, from about 0.05% w/w to about 20% w/w or preferably from about 0.1% w/w to about 10% w/w, of the composition. Some active substances may thus suitably be present in an amount of up to about 50% w/w of the composition, whereas the active substance may also, depending on the nature and strength of the active substance in question, be present in the composition in much smaller amounts.

Optionally, the therapeutic agents are mixed with a biodegradable polymeric substances such as: polylactic acid, polyglycolic acid, poly(lactic-co-glycolic) acid, polyanhydrides, blockpolymers, poly(orthoesters), poly(p-dioxanone), poly(alpha hydroxy butyric acid), and their co-polymers with polyethylene oxide or polypropylene oxide, and any mixtures thereof. The purpose of these polymer additives is to control the biodegradation rate and the drug release rate. In a general form of the invention any biodegradable polymeric additive, which may serve as carrier for a therapeutic agent is of relevance. The drug-biodegradable polymer system may be added to the composition in the form of liquid, large particles or as small nano- and micro-particles.

Method for Preparing a Composition According to the Invention

In a specific aspect, the invention relates to a method for the preparation of a pharmaceutical composition as defined in any of claims 25-69, which method comprises dispersing a mixture of i) one or more biodegradable hydrating ceramics in powder form, and ii) one or more expandable agents, in iii) an aqueous medium, wherein either the mixture of i) and ii), or iii) further comprises iv) one or more therapeutically, prophylactically and/or diagnostically active substances. The pharmaceutical composition is an injectable and in vivo solidifying composition for controlled release of the active substance.

Other embodiments appear from the appended claims to which reference is made. The details and particulars mentioned above under the main aspect apply mutatis mutandis to the other aspects of the invention.

Example

Prostate Cancer

A specific example of the usefulness of a composition according to the present invention is a composition containing an anti-cancer drug substance without limiting the invention to use in the treatment of prostate cancer or to compositions containing hydroxyflutamide as an active substance. The principal application of the present invention is for treatment of prostate diseases, primarily cancer and prostate hyperplasia (enlarged prostate). Some background to this field is provided first.

There are malignant and non-malignant tumours. Cancers and Sarcomas are malignant tumours, characterised by a non-controlled cell growth, and by the ability to invade and seed metastasis.

For men, prostate cancer is the most common type of cancer; it is today a leading lethal malignancy with increasing incidence worldwide. Prostate cancer patients can develop a resistance to anti-hormonal treatments (a so called androgen-independent disease), which remains the main obstacle to improved life expectancy. Existing systemic hormonal treatments only improve survival with a few years.

The function of the prostate gland is to secrete the milky substance of seminal fluid. Before puberty, this function does not exist and the gland is very small. Unlike many organs the growth of the prostate gland continues throughout the lifespan, often resulting in a benign prostatic hyperplasia of the gland.

The prostate is located anteriorly to the rectum. Above the prostate gland is the urinary bladder and below the urogenital diaphragm. The seminal vesicles form the ejaculatory ducts and enter the gland in a posterio-lateral direction and emerge in the urethra in approximately the middle of the gland. The gland is covered by a fibrotic capsule and has an elastic consistency.

The frequency of prostate cancer has stimulated the search for improved therapeutic agents and treatment procedures, e.g. novel anti-androgenic agents, prostate cancer gene therapy, immunotherapy. An important factor for a successful outcome of many of these new, or the more established therapeutic approaches, is ensuring sufficient local and sustained effect of the therapeutic substance within the tumour tissue, while minimising systemic effects.

Treatment Options

The treatment options for prostate cancer can be grouped into four broad categories: observation (for elderly patients and those with co-morbidities), anti-cancer therapy (for example hormone or anti-hormone, anti-metabolites, cytotoxic agents), surgery (radical prostatectomy), and radiotherapy (external-beam radiotherapy, brachytherapy, i.e. local placement of radioactive sources, or both).

The prostate is a hormone-responsive organ; this is the basis for treatments that either reduce serum and intracellular testosterone or block the actions of this hormone. Many anti-hormonal agents act to inhibit production of or block the action of testosterone. Examples of hormonal or ant-hormonal agents are oestrogens, progestagens, gonadotropin-releasing hormone analogues, adrenal and prostate enzyme synthesis inhibitors, inhibitors of membrane efflux and membrane transport proteins, gestagenes and antigestagenes, androgens and antiandrogens. Common is a combination of an antiandrogen with a gonadotropin-releasing hormone analogue to provide total blockade of androgens.

Also alternative methods for treating prostate diseases have been developed. Some are based on the intramuscular or subcutaneous application of sustained drug delivery depot formulations containing the selected drug as one component. Also repeated intraprostatic and intralesional injection of therapeutic compounds has been described. These methods have the disadvantages of producing either prolonged systemic exposure to high doses of formulations, or to require repetitive injections over substantial periods of time, respectively.

Disadvantages with present hormonal/anti-hormonal therapies of prostate cancer Common side-effects of systemically administered hormonal/anti-hormonal therapies are hot flushes, loss of libido or erectile function, weight gain, gynaecomastia, liver inflammation, and osteoporosis. These troublesome side effects remain major obstacles to hormonal dosing, and must be balanced against the long-term benefits.

The most commonly used oral antiandrogen therapy today is biclutamide (Casodex). It is used alone for early non-metastatic disease. The side effect spectrum of all clinically used antiandrogens includes diarrhea, breast enlargement, nausea, impotence, decreased libido, abdominal pain, flatulence, tiredness, asthenia, osteoporosis and sweating, and a decreased quality of life.

These side effects of the anti-cancer chemotherapy are to a major extent due to high levels of the active drug in the systemic circulation and different tissues outside the cancer tissue in the prostate. Importantly, none of these side effects are related to, or mediated by, the local drug action in the prostate tissue.

In view of the methods described above for treatment of prostate cancer, there is a need for improved procedures and formulations to optimise the effects of hormonal/anti-hormonal and other anticancer agents. Such better treatments would reduce the need for surgery and radio-treatments, and minimise the spectrum of side effects.

However, also the drug treatment of many other types of cancer as well as other diseases in soft tissue in humans and any other mammals would benefit from the sustained release formulation of the invention, both for local and systemic delivery.

Now focusing on a suitable active substance for use in the treatment of prostate cancer, 2-hydroxy-flutamide. In a pharmaceutical composition of the invention a controlled release profile for 2-hydroxy-flutamide, shall fulfil the therapeutic concentration, which is within the interval 0.001-1000 μM, preferably 0.01-100 μM or more preferably 0.05-5.0 μM, and the treatment time for one dose is at least 3-6 months or more.

The active substance may be implanted into the prostate tissue through the urethra by conventional cystoscopy or other technique for injections/implantation such as ultrasound, MR (magnetic resonance), X-ray, CT (computer tomography), manual guidance through the rectum, etc.

The treatment response may be monitored by assaying PSA (prostate specific antigen) in plasma (a well-established bio-marker for this disease), i.e. the same diagnostic systems used in routine practice in the management and follow-up of patients with prostate cancer. If a local treatment fails to lower the PSA level, the risk of metastatic tissue increases.

The following examples are intended to illustrate the invention without limiting it thereto.

BRIEF DESCRIPTION OF DRAWINGS

The invention will now be exemplified in further detail below with reference to the enclosed drawings.

EXAMPLES

Example 1

Compositions Having Varying Water Content

Figure 1:
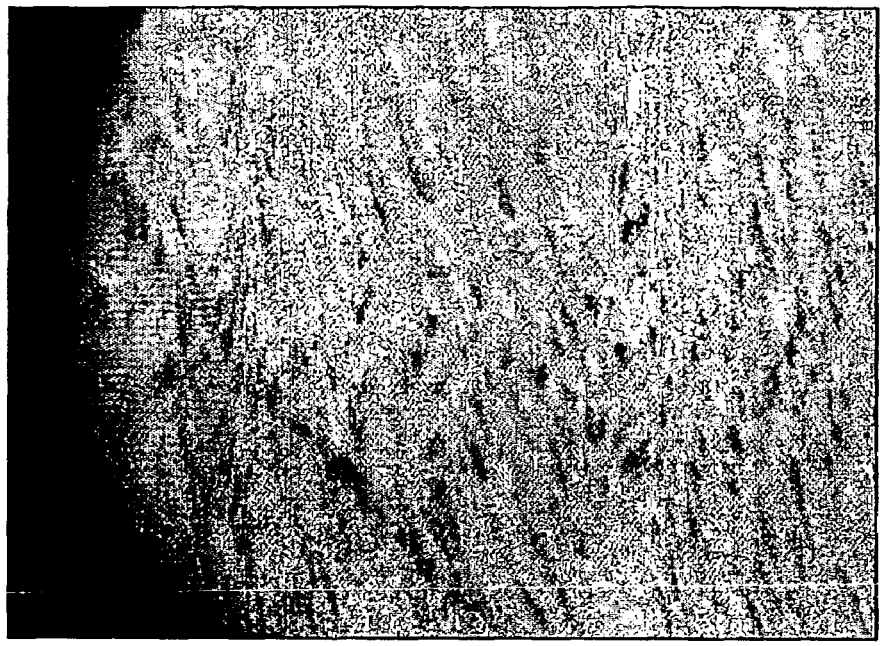
FIG. 1: Optical microscopy image of polished plat surface of a calcium sulphate-water pellet as in Example 1. At a magnification of 50× no porosity is visible.

Compositions based on calcium sulphate, water and hydroxyflutamide were prepared by mixing powder of calcium sulphate hemi-hydrate ($CaSO_4 \cdot 1/2H_2O$) from Riedel-deHaën (CAS-no 10034-76-1), laboratory de-ionised water and powder of 2-hydroxyflutamid (HF). The compositions contain the following:

| Ingredient | amount (g) | concentration in the final composition (% w/w) |
| --- | --- | --- |
| Composition 1 | | |
| Calcium sulphate | 0.396 | 79.2 |
| Hydroxyflutamide | 0.004 | 0.8 |
| Water | 0.100 | 20.0 |
| Composition 2 | | |
| Calcium sulphate | 0.296 | 59.2 |
| Hydroxyflutamide | 0.004 | 0.8 |
| Water | 0.200 | 40.0 |

Pastes were prepared with two different water contents: Calcium sulphate with 20% water and 0.8% of HF, and calcium sulphate with 40% water and 0.8% of HF.

The materials were prepared as pellets with a size of diameter 4 mm and thickness 1.0 mm. Three pellets were prepared of each composition. The pellets were left to harden for 1 hr after preparation. Each pellet was incubated individually in a tube containing 10 ml of saline solution (9 mg/ml concentration) and kept in a water bath at 37° C. for a total of 14 days. A sample of 0.5 ml of the saline was taken every 24 hours and the volume was replaced with 0.5 ml of fresh saline solution. The concentration of HF in the saline solution was measured in each sample with a HPLC-method with UV-detection.

The overall porosities of both compositions were between 30 and 50% as estimated with a Zeiss Scanning electron microscope on cross-sections of dried samples.

After 4 days, the more water rich composition (40%) had released an average of 24%, and the samples with 20% water had released about 20% of the HF. However, after 15 days both compositions had released about 50% of their HF.

During these 15 days the degradation of the calcium sulphate is negligible.

In conclusion, the variation in water content has a small but measurable effect on the release rate during the initial stage of the release. Higher water content presumably produces a slightly higher porosity, which might explain this initial difference. However, no difference in porosity could be measured. After significant amounts of HF have been released, there is no more any significant difference in the release rate.

It is believed that the release is largely controlled by diffusion through the porosity.

Example 2

A Composition According to the Invention Having Varying Content of a Hydrophilic Release-Modifying Agent Samples were prepared as in Example 1 but with an addition of methylcellulose from Fluka (Product no. 64632). Prior to use, the methylcellulose was dissolved in de-ionised water at a concentration of 50 g per liter of water. The solution was heated to 70° C. to speed up the dissolution of methylcellulose. It is contemplated that a saturated methylcellulose-water gel is located in the micro-porosity of the calcium sulphate structure during curing of the pastes, and inhibit or delay diffusion of the active substance through the micro-porous structure. A similar effect may be achieved by using methylcellulose in a micronised form (having a particle size in the micron area or less).

Compositions with 6 and 14% of cellulose as measured by weight were prepared.

| Ingredient | amount (g) | concentration in the final composition (% w/w) |
| --- | --- | --- |
| Composition 3 | | |
| Calcium sulphate | 0.266 | 53.2 |
| Hydroxyflutamide | 0.004 | 0.8 |
| Methylcellulose | 0.030 | 6.0 |
| Water | 0.200 | 40.0 |
| Composition 4 | | |
| Calcium sulphate | 0.226 | 45.2 |
| Hydroxyflutamide | 0.004 | 0.8 |
| Methylcellulose | 0.070 | 14.0 |
| Water | 0.200 | 40.0 |

After 4 days, the release was reduced (cf. Example 1) to about 16% for the composition with 6% methylcellulose, and to 14% for the samples with 14% cellulose. After 15 days the release is about 50%, i.e. of the same order of magnitude as for the compositions without cellulose in Example 1.

It is contemplated that methylcellulose is entrapped in the porous structure of calcium sulphate and hinders the diffusion of the HF during an initial stage, but with time also methylcellulose is dissolved in the saline solution and, accordingly, the diffusion hindrance caused by the cellulose ceases.

In conclusion, a water-soluble, but slowly soluble, substance may be used as a release-modifying agent, especially, if it is desired to decrease the initial release rate.

Further tests are focused on the absorption of water into the porosity of cured pellets, as a measure of the water penetration of the composition.

Example 3

A Composition According to the Invention Having Varying Content of a Hydrophobic Release-Modifying Agent Pellets were prepared as in Example 1. The compositions include calcium sulphate hemi-hydrate, de-ionised water and silicone oil of viscosity 12.500 cp (type Med 420 from Nusil Technology). The oil was first dispersed in the de-ionised water by heavy shaking, and further distributed during the massaging of the formed paste.

Water absorption was evaluated as the increase in weight of the pellets before and after soaking for 10 minutes in de-ionised water, and carefully dried on a paper tissue.

Compositions were prepared with two different silicone oil contents: 1% and 10% as measured by weight.

| Ingredient | amount (g) | concentration in the final composition (% w/w) |
|---|---|---|
| Composition 5 | | |
| Calcium sulphate | 0.391 | 78.2 |
| Hydroxyflutamide | 0.004 | 0.8 |
| Silicone oil | 0.005 | 1.00 |
| Water | 0.100 | 20.0 |
| Composition 6 | | |
| Calcium sulphate | 0.346 | 69.2 |
| Hydroxyflutamide | 0.004 | 0.8 |
| Silicone oil | 0.050 | 10.0 |
| Water | 0.100 | 20.0 |

The pellets were first cured for 1 hr and thereafter left to dry for 24 hrs in a silica gel autoclave before testing of water absorption.

A pellet without silicon oil absorbs between 23% and 40% of water as measured by volume and related to the volume of a pellet. An amount corresponding to 1% w/w of silicone oil did not affect the water absorption measurably in these tests. An amount corresponding to 10% w/w of oil however reduced the water absorption significantly to 5-10% as measured by volume.

It is believed that the silicone oil, if well dispersed fills the porosity of the cured pellets and repels water to penetrate.

Accordingly, the release of the active substance from the cured pellets is decreased compared to the results obtained in Example 2 using a hydrophilic release-modifying agent. In conclusion, a hydrophobic release-modifying agent may be used to decrease the release rate during a long period of time.

Example 4

A Composition According to the Invention Having Varying Content of a Low Solubility Hydrophilic Release-Modifying Agent Pellets were prepared as in Example 3, but without the oil. Instead 6% and 18% calcium silicate (corresponding to 10 and 30% by weight as related to the calcium sulphate powder) was added to the compositions. The following compositions were made:

| Ingredient | amount (g) | concentration in the final composition (% w/w) |
|---|---|---|
| Composition 7 | | |
| Calcium sulphate | 0.266 | 53.2 |
| Hydroxyflutamide | 0.004 | 0.8 |
| Calcium silicate | 0.030 | 6.0 |
| Water | 0.200 | 40.0 |
| Composition 8 | | |
| Calcium sulphate | 0.206 | 41.2 |
| Hydroxyflutamide | 0.004 | 0.8 |
| Calcium silicate | 0.090 | 18.0 |
| Water | 0.200 | 40.0 |

The same water absorption test as in Example 3 revealed that addition of calcium silicate reduced the water absorption to about 25-30% for the compositions with 6% w/w of calcium silicate, and to about 15-20% for the samples with 30% w/w of calcium silicate.

Due to the high water binding capability, calcium silicate will react with water and form an insoluble hydrate in the form of crystals. These crystals or otherwise precipitated materials locate in the porous structure of the cured calcium sulphate pellet.

In conclusion, a hydrophilic and strongly water binding hydrating ceramic substance that may be transformed into a poor water-soluble hydrate substance can be used as an alternative to the hydrophobic substances (such as silicone oil mentioned above) as a release modifying agent.

Example 5

Composition According to the Invention Containing a Foaming Agent

Paste of only calcium sulphate and 40% water were prepared as in Example 1 with 40% water. To 0.5 g of the paste 1 mg of sodium bicarbonate was added and mixed thoroughly. The paste was left to cure. During curing a foam-like structure was formed. This is the result of the bicarbonate generating gas, as it is wetted.

Figure 2:
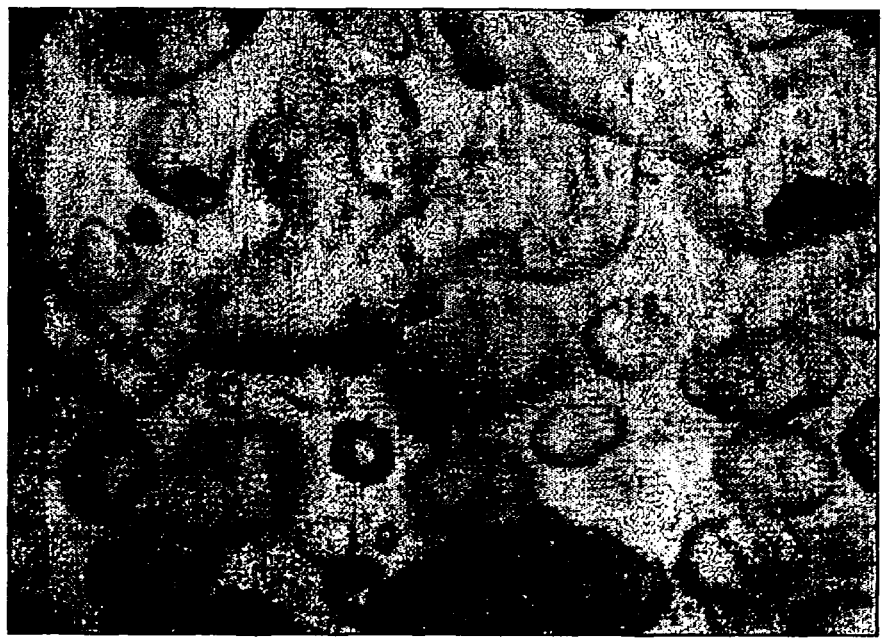
FIG. 2: Optical microscopy image of polished surface of a calcium sulphate-water pellet with sodium bicarbonate as in Example 5. At a magnification of 50× openings are visible.

The macroscopic appearance of this foamed material was characterised by openings having a size in the range of 0.5-1.5 mm and an overall porosity of 60-80%. This open structure is at a much larger scale than the micro-porosity obtained in examples 1-4 (relating to the calcium sulphate itself), see FIGS. 1 and 2 herein.

Accordingly, it is possible to obtain a larger apparent surface area of the calcium sulphate pellet and thereby, adjusting the surface area exposed to body fluids and in turn to erosion after administration to a body.

Example 6

Composition According to the Invention Containing a Foaming Agent

Paste of only calcium sulphate and water were prepared as in Example 1 with 40% water. To 0.5 g of the pastes 10 mg of water peroxide (30% concentration from Fluka) was added. The paste was left to cure; a foam-like structure was formed.

Similarly as in Example 5, the macroscopic porosity of this foamed material was characterised by openings in the range of 0.5-1.5 mm and an overall porosity of 60-80%.

Example 7

Erosions Rates of Composition According to the Invention

The erosion/dissolution rate over time was measured for bodies kept in saline solution (9 mg/ml) at room temperature for three different compositions. The first composition (A)

was prepared from calcium sulphate and water in the proportions 3 units of powder to 2 units of water by mass. This creates a structure similar to that in FIG. 1.

A second composition (B) based on the above composition (A) but with 1 mg of sodium bi-carbonate was prepared. This composition has a large open porosity characterised by pores in the range of 0.5-1.5 mm in diameter. The structure is similar to that in FIG. 2.

A third composition (C) was prepared based on the composition (A) but with an addition of 10 mg of silicon oil of 12500 cp viscosity (type Med 420 from Nusil Technology).

From these compositions flat coins of 15 mm diameter and a thickness of 2.0 mm were shaped and left to cure for 10 hrs. The coins were left in 50 ml tubes with saline (9 mg/ml). The dissolution of the coins was measured by weighing after 24 hrs, 48 hrs, 4 days and 7 days. Prior to each measurement the coins were wetted and the exterior dried with a dry tissue. The relative weight losses were as follows:

| Composition | Weight start | 24 hrs | 48 hrs | 4 days | 7 days |
|---|---|---|---|---|---|
| A | 1 | 0.988 | 0.937 | 0.915 | 0.889 |
| B | 1 | 0.932 | 0.853 | 0.753 | 0.655 |
| C | 1 | 0.990 | 0.947 | 0.922 | 0.900 |

The experiments show that the larger surface area of an open or disintegrated structure provides a higher dissolution/erosion rate. The example also illustrates that the addition of silicon oil, which reduces the water up-take as illustrated in Example 3, has a very small effect on the erosion rate. Accordingly, sealing of the micro-porous structure of a ceramic and thereby avoiding leakage of any active substance there from, is an appropriate means to control the overall release of active substance from the composition, namely by means of erosion.

Example 8

Method to Evaluate Release Rates from the Compositions

This example describes a suitable method for the evaluation of the release rate from compositions of the invention.

Composition according to example 1, composition 2, with three different 2-hydroxyflutamide (HT) concentrations, was tested in a dog study. The concentration profile of HT in prostate tissue in male dogs after local administration of the composition was investigated at different time points. Also a reference implant without HT was implanted in one dog.

Three male dogs are given 30, 60 or 120 mg of 2-hydroxyflutamide by local implant delivery system in the prostate tissue; the total implantation time was 3 weeks.

The implant drug delivery system was inserted locally into the prostate tissue through sterile needles during rectal ultrasound guidance. The animals were under anesthesia during the insertion procedure.

Blood samples were taken every day for the first week and then once a week for the remaining weeks. Plasma samples were collected in tubes with EDTA and the plasma were transferred to microtubes of 2 ml, (sterile kryotubes from Sarstedt; No. 694.005).

The quantification of the parent drug, 2-hydroxyflutamide, in the plasma and tissue samples, was done by HPLC-MS analysis.

Figure 3:
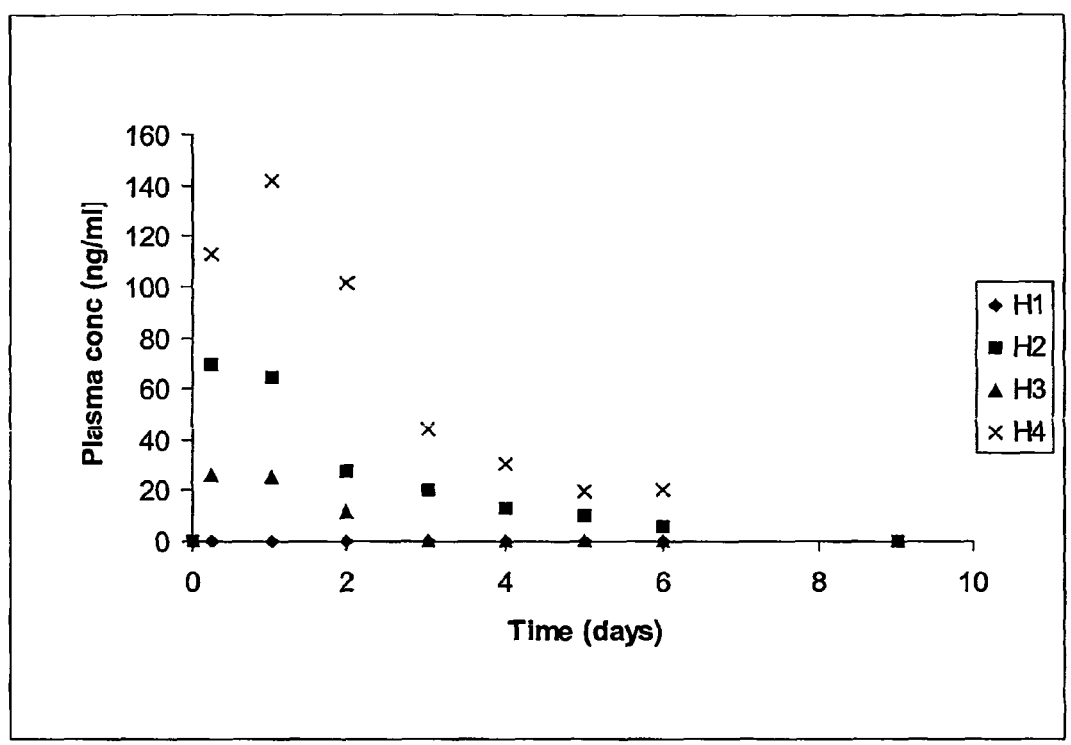
FIG. 3: Graph showing the plasma concentrations of 2-hydroxyflutamide in dog plasma after three different doses of 2-hydroxyflutamide (H2, H3 and H4) in a calcium sulphate-water implant in dog prostate tissue. One dog (H1) was used as control and was dosed an implant without 2-hydroxyflutamide.

The graphs in FIG. 3 show the plasma concentrations of 2-hydroxyflutamide in dog plasma after three different doses of 2-hydroxyflutamide as an implant in dog prostate tissue (H2, H3 and H4). Dog 1 (H1) was used as control and was only dosed an implant without 2-hydroxyflutamide.

The extended plasma profiles over 3-6 days shows, that the release rates of 2-hydroxyflutamide correlate well with in-vitro release rates in Example 1.

The invention claimed is:

1. An injectable pharmaceutical composition comprising:
i) one or more biodegradable hydrating ceramics;
ii) one or more expandable agents, wherein the expandable agent is present in the composition at a concentration of at least about 0.1% w/w to about 2.5% w/w;
iii) a sorbed aqueous medium wherein the sorbed aqueous medium is present in the composition at a concentration of at the most about 30% w/w to about 60% w/w of the total composition; and
iv) one or more therapeutically and/or diagnostically active substances, which is an androgen, an anti-androgen, an oestrogen, an anti-oestrogen, a gestagen, an anti-gestagen, an oligonucleotide, a progestagen, a gonadotropin-releasing hormone, a gonadotropin inhibitor, an adrenal and/or prostate enzyme inhibitor, a membrane efflux and/or membrane transport protein, an immune system modulator, an angiogenesis inhibitor, or combinations thereof, which in solid form has a ruptured structure, and wherein the composition solidifies within 20 minutes or less when stored at 37° C.

2. A pharmaceutical composition according to claim 1, wherein the active substance is flutamide, hydroxy-flutamide, cyproteron, nilutamide or bicalutamide or a mixture thereof.

3. A pharmaceutical composition according to claim 1, wherein the active substance is a combination of an anti-androgen and a gonadotropin-releasing hormone.

4. A pharmaceutical composition according to claim 1, which in solid form has a foam-like structure with openings, wherein at least 50% or more of the openings have a maximum width of at least about 0.1 mm.

5. A pharmaceutical composition according to claim 4, wherein, at least 60%, to 90% of the openings have a maximum width of at least about 0.1 mm.

6. A pharmaceutical composition according to claim 5, wherein the openings have a maximum width of at least about 0.2 mm to at least about 0.5 mm.

7. A pharmaceutical composition according to claim 5, wherein the openings have a largest width of at least about 0.6 mm to about 2 mm.

8. A pharmaceutical composition according to claim 1, wherein the surface area of an opening in cross sectional view having a maximum width of at least about 0.1 mm is at least about $3 \times 10^{-8}$ m$^2$ to about $5 \times 10^{-6}$ m$^2$.

9. A pharmaceutical composition according to claim 1, which in solid form has a ruptured structure obtained by disintegration into two or more parts.

10. A pharmaceutical composition according to claim 9, wherein the two or more parts have an external surface area that is at least about twice to about a thousand times as large as that of the composition before disintegration.

11. A pharmaceutical composition according to claim 1, wherein the biodegradable hydrating ceramic is selected from the group consisting of non-hydrated or hydrated calcium sulphate, calcium phosphate, calcium carbonate, calcium fluoride, calcium silicate, magnesium sulphate, magnesium phosphate, magnesium carbonate, magnesium fluoride, magnesium silicate, barium sulphate, barium phosphate, barium carbonate, barium fluoride, barium silicate, or mixtures thereof.

12. A pharmaceutical composition according to claim 1, wherein the biodegradable hydrating ceramic is non-hydrated or hydrated calcium sulphate.

13. A pharmaceutical composition according to claim 1, wherein the biodegradable hydrating ceramic employed in the preparation of the composition is in the form of a powder.

14. A pharmaceutical composition according to claim 13, wherein the powder has a mean particle size of at the most about 10 μm to about 75 μm.

15. A pharmaceutical composition according to claim 1, wherein the expandable agent is a gas-forming agent, a swelling agent, a gelling agent or a disintegrant.

16. A pharmaceutical composition according to claim 15, wherein the expandable agent is a gas-forming agent selected from the group consisting of alkali metal carbonates, alkali metal hydrogen carbonates, hydrogen peroxide and mixtures thereof.

17. A pharmaceutical composition according to claim 15, wherein the expandable agent is a swelling agent, a gelling agent, a disintegrant, or mixtures thereof.

18. A pharmaceutical composition according to claim 1; in liquid or semi-solid form.

19. A pharmaceutical composition according to claim 1, wherein the ruptured structure has a shape selected from the group consisting of beads, tubes, polygons, spheres, stars, cubes, or mixtures thereof.

20. A pharmaceutical composition according to claim 1, wherein the active substance is homogeneously dispersed in the biodegradable hydrating ceramic.

21. A pharmaceutical composition according to claim 1, configured for parenteral use.

22. A pharmaceutical composition according to claim 1, wherein the one or more biodegradable hydrating ceramics, the expandable agent and the one or more active substance are homogeneously dispersed in water so that the hydrating ceramic, the expandable agent and/or the active substance sorbs water.

23. A pharmaceutical composition according to claim 1, wherein the one or more biodegradable hydrating ceramics have a microporous structure.

24. A pharmaceutical composition according to claim 23, wherein at least part of the microporous structures is sealed with a pore-sealing agent.

25. A pharmaceutical composition according to claim 23, wherein at least 50% or more of the microporous structures is sealed with a pore-sealing agent.

26. A pharmaceutical composition according to claim 24, wherein the pore-sealing agent is a hydrophobic agent, a hydrophilic agent, a water-absorbing agent, or mixtures thereof.

27. A pharmaceutical composition according to claim 24, wherein the pore-sealing agent is a hydrophobic agent that is selected from the group consisting of silicone oil, silicon rubber, waxes, paraffinic hydrocarbons, polyvinylalcohols, ethyl cellulose, and mixtures thereof.

28. A pharmaceutical composition according to claim 24, wherein the pore-sealing agent is a hydrophilic agent that is selected from the group consisting of methylcellulose, hyaluronic acid, dextran, poly-ethylene glycol (PEG), and mixtures thereof.

29. A pharmaceutical composition according to claim 24, wherein the pore-sealing agent is a water-absorbing agent that is selected from the group consisting of water glasses, silica gel, sodium phosphate, and mixtures thereof.

30. A pharmaceutical composition according to claim 24, wherein the concentration of the pore-sealing agent in the composition is about 30% w/w or less of the final composition.

31. A pharmaceutical composition according to claim 1, wherein the active substance is controllably released from the composition.

32. A pharmaceutical composition according to claim 31, wherein at most about 10% w/w of the active substance contained in the composition is released 5 days or more after implantation to a human.

33. A pharmaceutical composition according to claim 31, wherein at the most about 50% w/w of the active substance contained in the composition is released 1 month or more after implantation to a human.

34. A pharmaceutical composition according to claim 31, wherein at the most about 75% w/w of the active substance contained in the composition is released 1.5 month or more after implantation to a human.

35. A pharmaceutical composition according to claim 31, wherein at the most about 100% w/w of the active substance contained in the composition is released 2 month or more after implantation to a human.

36. A pharmaceutical composition according to claim 31, wherein at the most about 10% w/w of the active substance contained in the composition is released after 2 days or more when tested in an in vitro dissolution test according to Ph. Eur protocol.

37. A pharmaceutical composition according to claim 31, wherein at the most about 50% w/w of the active substance contained in the composition is released after 1 month or more when tested in an in vitro dissolution test according to Ph. Eur protocol.

38. A pharmaceutical composition according to claim 31, wherein at the most about 75% w/w of the active substance contained in the composition is released after 1.5 month or more when tested in an in vitro dissolution test according to Ph. Eur protocol.

39. A pharmaceutical composition according to claim 31, wherein at the most about 100% w/w of the active substance contained in the composition is released after 2 month or more when tested in an in vitro dissolution test according to Ph. Eur protocol.

40. A composition in particulate form for use in the preparation of an injectable pharmaceutical composition as recited in claim 1, the composition comprising:
  i) one or more biodegradable hydrating ceramics in powder form;
  ii) one or more expandable agents, in an amount sufficient to be present in the injectable composition at a concentration of at least about 0.1% w/w/ to about 2.5% w/w; and
  iii) one or more therapeutically and/or diagnostically active substances, which is an androgen, an anti-androgen, an oestrogen, an anti-oestrogen, a gestagen, an anti-gestagen, an oligonucleotide, a progestagen, a gonadotropin-releasing hormone, a gonadotropin inhibitor, an adrenal and/or prostate enzyme inhibitor, a membrane efflux and/or membrane transport protein, an immune system modulator, an angiogenesis inhibitor, or combinations thereof.

41. A method for the preparation of an injectable pharmaceutical composition as recited in claim 1, comprising;
  a) dispersing a mixture of: i) one or more biodegradable ceramics in powder form, and ii) one or more expandable agents in an amount sufficient to be present in the injectable composition at a concentration of at least about 0.1% w/w to about 2.5% w/w; in an amount of a sorbed aqueous medium sufficient to be present in the injectable composition at a concentration of at the most about 30% w/w to about 60% w/w of the total composition; and b) adding one or more therapeutically or diagnostically active substances, which is an androgen, an anti-androgen, an oestrogen, an anti-oestrogen, a gestagen, an anti-gestagen, an oligonucleotide, a progestagen, a gonadotropin-releasing hormone, a gonadotropin inhibitor, an adrenal and/or prostate enzyme inhibitor, a membrane efflux and/or membrane transport protein, an immune system modulator, an angiogenesis inhibitor, or combinations thereof, such that in solid for said injectable composition has a ruptured structure, and wherein the injectable composition solidifies within 20 minutes or less when stored at 37° C.

42. A method for treatment of a subject suffering from a prostate disease, comprising administering to the subject an injectable composition as recited in claim 1.

43. A method according to claim 42, wherein the prostate disease is prostate cancer or prostate hyperplasia.

44. A method according to claim 42, wherein the active substance is flutamide, hydroxy-flutamide, cyproteron, nilutamide or bicalutamide or a mixture thereof.

45. A method according to claim 42, wherein the active substance is a combination of anti-androgen and a gonadotropin-releasing hormone.

46. A method according to claim 42, wherein the active substance is hydroxyflutamide.

47. A method according to claim 42, wherein the active substance is hydroxyflutamide and a plasma concentration of from 0.001 to 1000 µM hydroxyflutamide is obtained in the subject after administration thereof.

48. A method according to claim 42, wherein the active substance is hydroxyflutamide and the treatment time for one dose is at least 3-6 months.

49. A method according to claim 42, wherein the composition solidifies in vivo after administration.

* * * * *